(12) United States Patent
Goldberg et al.

(10) Patent No.: US 10,117,749 B2
(45) Date of Patent: Nov. 6, 2018

(54) SUBTALAR JOINT IMPLANT (71) Applicant: UCL BUSINESS PLC, London (GB)

(72) Inventors: Andy Goldberg, Stanmore (GB); Gordon Blunn, Stanmore (GB)

(73) Assignee: UCL Business, LLC (GB)

( * ) Notice: Subject to any disclaimer, the term of this patent is extended or adjusted under 35 U.S.C. 154(b) by 21 days.

(21) Appl. No.: 15/517,090

(22) PCT Filed: Sep. 11, 2015

(86) PCT No.: PCT/GB2015/052634
§ 371 (c)(1),
(2) Date: Apr. 5, 2017

(87) PCT Pub. No.: WO2016/055762
PCT Pub. Date: Apr. 14, 2016

(65) Prior Publication Data
US 2017/0246004 A1 Aug. 31, 2017

(30) Foreign Application Priority Data
Oct. 6, 2014 (GB) .................................. 1417618.4

(51) Int. Cl.
*A61F 2/42* (2006.01)
*A61F 2/30* (2006.01)

(52) U.S. Cl.
CPC ...... *A61F 2/4202* (2013.01); *A61F 2002/304* (2013.01); *A61F 2002/3021* (2013.01); *A61F 2002/3022* (2013.01); *A61F 2002/3065* (2013.01); *A61F 2002/30378* (2013.01); *A61F 2002/30657* (2013.01); *A61F 2002/30662* (2013.01); *A61F 2002/4207* (2013.01); *A61F 2002/4217* (2013.01)

(58) Field of Classification Search
CPC ................. A61F 2002/4207; A61F 2002/4217
See application file for complete search history.

(56) References Cited

U.S. PATENT DOCUMENTS

2010/0280625 A1* 11/2010 Sanders ................ A61F 2/4202
623/21.18
2014/0039506 A1 2/2014 Ringus et al.
2014/0128985 A1 5/2014 Sanders et al.

FOREIGN PATENT DOCUMENTS

CN 201001789 Y 1/2008
EP 1433444 A1 6/2004
(Continued)

OTHER PUBLICATIONS

Fournol, S., "L'arthroplastie totale sous-talienne Resultats et bilan d'une serie de 100 protheses", Medical Chirurgie Pied, vol. 15, pp. 67-71, 1999. (English translation of abstract).
(Continued)

*Primary Examiner* — David H Willse
(74) *Attorney, Agent, or Firm* — Vos-IP, LLC (57) ABSTRACT

A subtalar joint implant (20) is disclosed for replacing a natural subtalar joint existing between the talus (102) and calcaneum (104) bones of a patient. In an embodiment the implant comprises talar (22) and calcaneal (24) portions that are configured to slide over each other in the implanted state. The implant is shaped so that the sliding is constrained to trajectories that involve pivoting of the talar portion relative to the calcaneal portion about a pivot point (36) or a line (38) of pivot points.

20 Claims, 8 Drawing Sheets

(56) References Cited

FOREIGN PATENT DOCUMENTS

FR 2669215 A1 5/1992
WO 2013025194 A1 2/2013

OTHER PUBLICATIONS

International Search Report issued in International Application No. PCT/GB2015/052634 filed Sep. 11, 2015 and dated Dec. 4, 2015.

* cited by examiner

SUBTALAR JOINT IMPLANT

BACKGROUND OF THE INVENTION

The present invention relates to a subtalar joint implant for replacing a natural subtalar joint existing between the talus and calcaneum bones of a patient. The present invention is directed in particular to a subtalar joint implant that is reliable and provides realistic emulation of the functions of a healthy natural subtalar joint.

Arthritis is a common chronic condition as people become older, and with an ageing population the healthcare costs associated with osteoarthritis will continue to rise. Joint replacement is a successful treatment for hip, knee, shoulder and ankle arthritis allowing restoration of function for patients. Such joint replacements are able to provide realistic emulation of the functions of the non-damaged joints.

End-Stage ankle and hindfoot arthritis is a major problem that has been shown to affect quality of life as much as end stage heart disease. At the time of writing it is estimated that up to 70,000 people are affected by subtalar joint arthritis in the UK alone. The commonest cause is posttraumatic, occurring in up to 16.9% of patients following a calcaneal fracture. Other non-traumatic causes include longstanding flat foot, tendon dysfunction and inflammatory arthritis. Aside from the use of painkillers, activity modification, and injections of steroids, there is only a single operative treatment at present—removal of the subtalar joints and fusion of the talus to the calcaneum (subtalar joint fusion). Fusion causes transmission of stresses to adjacent joints that might later fail. Although subtalar joint replacement has been attempted, it has not been successful, with early failure rates in the series of the first 100 of greater than 50% (Fournol S, Medical Chirurgie Pied 15: 67-71, 1999).

The creation of a subtalar joint replacement that is as functionally effective and reliable as the widely used hip and knee replacements is inhibited by the higher complexity of the subtalar joint and the lack of a consensus on a detailed understanding of the mechanics of the joint. The ankle complex comprises a number of bones articulating by joints between them. It is commonly thought that the majority of up and down movements (doriflexion/plantarflexion) take place at the true ankle joint, between the tibia and talus, whereas side to side balancing movements (inversion/eversion) are thought to take place at the subtalar joint, which is the joint between the talus and calcaneum (heel bone). However, it has proved difficult to construct a mechanical arrangement that emulates the function of the subtalar joint in a reliable and realistic manner.

CN201001789 and WO 2013/025194 A1 discloses examples of arrangements in which talar and calcaneal components of a subtalar joint prosthesis are configured to be slidable relative to each other in order to emulate function provided by a natural subtalar joint. The realism of the emulation is limited, however, because the sliding is not constrained in the same way as the movement allowed by the natural subtalar joint especially under load. Excessive and/or unnatural movement may lead to clinical instability and early failure of the prosthesis.

BRIEF SUMMARY OF THE INVENTION

It is an object of the invention to provide a subtalar joint implant that provides a more reliable and realistic emulation of the functions of a healthy natural subtalar joint.

According to an aspect of the invention, there is provided a subtalar joint implant for replacing a natural subtalar joint existing between the talus and calcaneum bones of a patient, the implant comprising: a talar portion configured to be rigidly attached to the talus; and a calcaneal portion configured to be rigidly attached to the calcaneum, wherein, where upper and lower directions are defined relative to the orientation of the implant when implanted in a weight bearing or standing patient: a first and a second region of a lower surface of the talar portion are configured to be in contact with respective first and second regions of an upper surface of the calcaneal portion during use; the first regions are shaped so as to allow sliding of the first region of the lower surface of the talar portion over the first region of the upper surface of the calcaneal portion; and the second regions are shaped so as to define a pivot point or line of pivot points and constrain said sliding of the first region of the lower surface of the talar portion over the first region of the upper surface of the calcaneal portion to trajectories that involve pivoting of the talar portion relative to the calcaneal portion about the pivot point or pivot points.

The combination of the relative sliding motion between the first regions and the constraining action of the pivot point or line of pivot points defined by the second regions provides a realistic emulation of the movement allowed by the natural subtalar joint in a non-loaded situation (e.g. as the foot is placed on an uneven surface and adapts to the shape of the floor).

Further, the inventors have realised that the poor performance of previous subtalar implants resulted from inadequate understanding of subtalar joint motion in the natural joint. The inventors have realised in particular that under tibiotalar vertical loading, the natural subtalar joint complex is in a close-packed position with maximum talar head surface contact in the acetabulum pedis. The component ligaments of the latter are under maximum tension and the posterior talocalcaneal surfaces are interlocked. The inventors have recognised that in this position (e.g. single leg mid stance) the subatalar joint has minimal motion and the majority of motion (inversion and eversion) takes place at the ankle joint (between the tibia and talus) or at the mid and forefoot. In contrast in a non-loaded situation (e.g. during heel strike), the majority of the inversion and eversion takes place at the subtalar joint, by rotation of the posterior facet about an axis passing through the middle facet (and constrained to pivot about the middle facet), allowing the foot to be positioned on an uneven surface prior to mid-stance. Experiments performed by the inventors assessing the motion of the hindfoot complex in human subjects in a loaded and unloaded situation revealed a significant reduction in total side-to-side motion (inversion/eversion) between loaded and unloaded situations.

The combination of the relative sliding motion between the first regions and the constraining action of the pivot point or line of pivot points defined by the second regions when unloaded emulates the movement of the natural joint. Under load the curved shapes of the first and second regions provides a large surface area of contact and friction which increases the stability of the construct reducing motion compared to the non loaded state, and hence stability of the construct, a further emulation of the natural joint.

In an embodiment the sliding of the first regions relative to each other is along a curved trajectory. The curved trajectory desirably emulates the curved trajectory followed by the relative movement between the talus and the calcaneum (particularly the posterior facets of the talus and calcaneus) in the natural subtalar joint. In an embodiment, the sliding of the first regions relative to each other constitutes rotation of the talar portion relative to the calcaneal portion about an axis that is fixed during at least a portion of an allowed range of sliding. This movement provides a good approximation of an important aspect of the movement found in the natural subtalar joint. In an embodiment, when viewed from above, said axis passes through said pivot point or pivot points or a region adjacent to the pivot point or pivot points that overlaps with one or both of the second regions. This movement enhances further the emulation of the movement found in the natural subtalar joint. Furthermore, the movements described above are realisable in an efficient and reliable manner using readily manufactured cooperating (e.g. complimentary) shapes. In an embodiment the movement is realised using cooperating frustums for the first regions and a ball and socket arrangement for the second regions.

In an embodiment, the materials and shapes of the first regions are configured such that the sliding of the first regions relative to each other is substantially prevented by friction between the first regions when 10% or more of the patient's weight is applied between the talar and calcaneal portions, optionally 20% or more, optionally 30% or more, optionally 40% or more, optionally 50% or more. Thus, the subtalar joint implant enters a locked state in which very little or no movement is possible between the talar and calcaneal portions, thus emulating the stability that is also present in the loaded state in the natural joint.

In an embodiment, the talar portion or the calcaneal portion comprises one or more abutment members configured to restrict the sliding of the first regions relative to each other to within a predetermined range. This further enhances the stability of the implant, both in the loaded and non-loaded states. The abutment regions restrict relative movement of the talar and calcaneal portions to be within a predetermined range. The predetermined range may for example correspond to the range of movement allowed by a typical natural subtalar joint. The restriction of movement by means of abutment members reliably prevents excessive relative movement between the talar portion and the calcaneal portion, which could be lead to clinical instability, which means that the subject feels unstable, and could fall over, leading to excessive stresses and potential injury. In addition, this excessive motion could lead to abnormal forces on the implants leading to implant-bone interface failure.

In an embodiment, the sliding of the first regions relative to each other constitutes rotation of the talar portion relative to the calcaneal portion and the one or more abutment members are configured to restrict the rotation to a range of 40 degrees or less, optionally 38 degrees or less, optionally 36 degrees or less, optionally 34 degrees or less, optionally 32 degrees or less, optionally 30 degrees or less, optionally 28 degrees or less, optionally 26 degrees or less, optionally 24 degrees or less, optionally 22 degrees or less, optionally 20 degrees or less. This type and range of movement closely corresponds to movement allowed by a typical natural subtalar joint.

In an embodiment, the talar and calcaneal portions are configured to be implanted in such a way that, when viewed from above, the first regions overlap with a region where the posterior facet of the subtalar joint was located prior to implantation of the implant. This arrangement provides particularly accurate emulation of the function of the natural joint because the first surfaces, which provide a sliding movement between the talus and calcaneum that is similar to that provided by the movement of the talus over the posterior facet of the subtalar joint, are located in the same or a similar position to the posterior facet.

In an embodiment, the talar and calcaneal portions are configured to be implanted in such a way that, when viewed from above, the second regions overlap with a region where the middle facet (and preferably where a central point of the middle facet) of the subtalar joint was located prior to implantation of the implant. This arrangement provides particularly accurate emulation of the function of the natural joint because the second surfaces, which constrain the sliding movement between the talus and calcaneum in a similar manner to the middle facet of the subtalar joint (namely such that the sliding occurs as a pivoting about a pivot point or line of pivot points) are located in the same or a similar position to the middle facet (and/or central point thereof). The arrangement is particularly effective when combined with the requirement for the first regions to overlap with a region where the posterior facet of the subtalar joint was located prior to implantation of the implant. This combination ensures that the orientation of the first surfaces (e.g. the axes of the frustums of the first surfaces when they are shaped as frustums) are aligned in a similar direction (e.g. an oblique orientation from postero-lateral to anteromedial) to the surfaces of the posterior facet of the subtalar joint. This orientation helps to ensure that inversion and eversion can occur through a similar trajectory to that achieved by a healthy, natural subtalar joint.

According to a further aspect of the invention, there is provided a method of implanting a subtalar joint implant for replacing a natural subtalar joint existing between the talus and calcaneum bones of a patient, wherein the implant comprises: a talar portion configured to be rigidly attached to the talus; and a calcaneal portion configured to be rigidly attached to the calcaneum, wherein, where upper and lower directions are defined relative to the orientation of the implant when implanted in a weight bearing or standing patient: a first and a second region of a lower surface of the talar portion are configured to be in contact with respective first and second regions of an upper surface of the calcaneal portion during use; the first regions of the lower and upper surfaces are shaped so as to allow sliding of the first region of the lower surface over the first region of the upper surface; and the second regions of the lower and upper surfaces are shaped so as to define a pivot point or line or pivot points and constrain said sliding of the first region of the lower surface over the first region of the upper surface to trajectories that involve pivoting of the talar portion relative to the calcaneal portion about the pivot point or pivot points, wherein the method comprises: preparing a space between the talus and calcaneum that is suitable for accommodating the implant; implanting the implant in the space in such a way that, when viewed from above, the first regions overlap with a region where the posterior facet of the subtalar joint was located prior to implantation of the implant and the second regions overlap with a region where the middle facet (and preferably where a central point of the middle facet) of the subtalar joint was located prior to implantation of the implant.

Implanting the implant in this way provides particularly accurate emulation of the function of the natural joint because the first surfaces, which provide a sliding movement between the talus and calcaneum that is similar to that provided by the movement of the talus over the posterior facet of the subtalar joint are located in the same or a similar position to the posterior facet, and the second surfaces, which constrain the sliding movement between the talus and calcaneum in a similar manner to the middle facet of the subtalar joint (namely to occur as a pivoting about a pivot point or line of pivot points) are located in the same or a similar position to the middle facet. The orientation of the first surfaces (e.g. the axes of the frustums of the first surfaces when they are shaped as frustums) are made to be aligned in a similar direction (e.g. an oblique orientation from posterolateral to anteromedial) to the surfaces of the posterior facet of the subtalar joint. This orientation helps to ensure that inversion and eversion can occur through a similar trajectory to that achieved by a healthy, natural subtalar joint.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
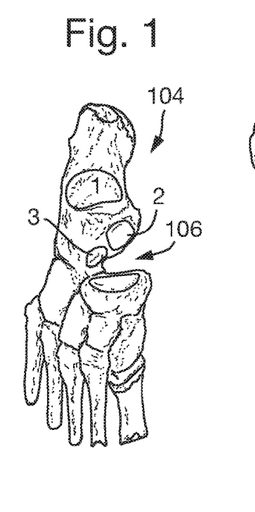
FIG. 1 is an anatomical top view of a foot, showing the calcaneum and navicular bone.
Figure 2:
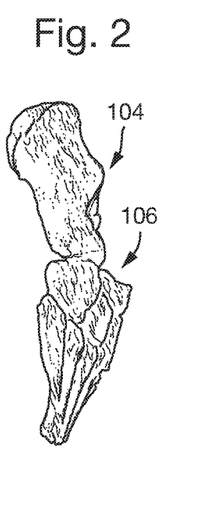
FIG. 2 is a side view from one side of the structure shown in FIG. 1.
Figure 3:
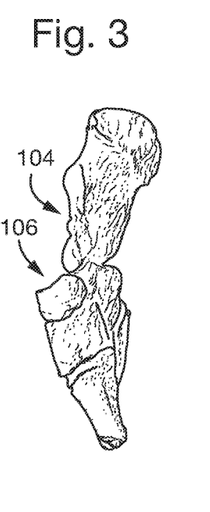
FIG. 3 is a side view from the other side of the structure shown in FIG. 1.
Figure 4:
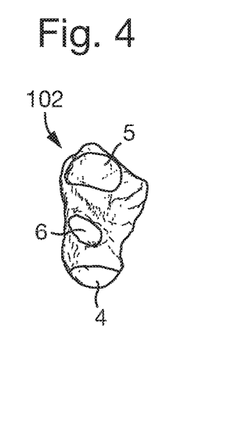
FIG. 4 is an anatomical bottom view of the talus.
Figure 5:
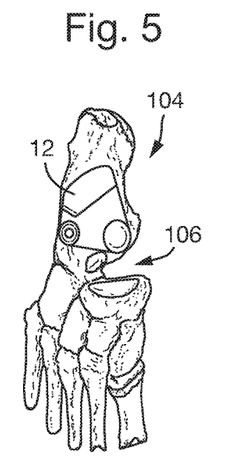
FIG. 5 corresponds to the view of FIG. 1 with a calcaneal portion of a subtalar implant attached to the calcaneum.
Figure 6:
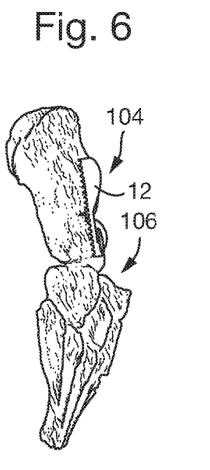
FIG. 6 is a side view from one side of the structure shown in FIG. 5.
Figure 7:
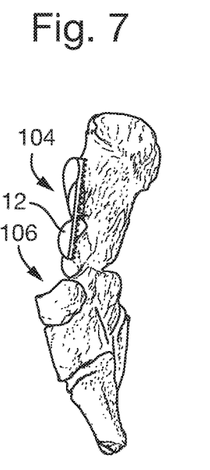
FIG. 7 is a side view from the other side of the structure shown in FIG. 5.
Figure 8:
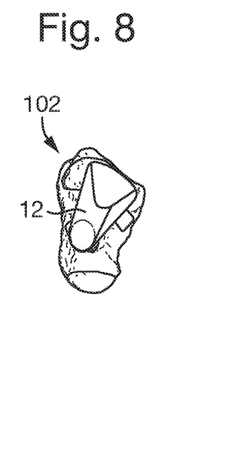
FIG. 8 is an anatomical bottom view of the talus with a talar portion of a subtalar implant attached to the talus.

FIGS. 1-4 illustrate an example subtalar joint. FIG. 1 is a view, along the distal direction, of the calcaneum (heel bone) 104 and the navicular bone 106. FIGS. 2 and 3 are respective side views of the structures shown in FIG. 1. FIG. 4 is a view, along the proximal direction, of the talus 102. The subtalar joint is the articulation between the talus 102 and the calcaneum 104 below the ankle joint. The subtalar joint is considered to be a plane synovial joint, also commonly referred to as a condyloid joint, between the talus 102 above, the calcaneum 104 below and the navicular bone 106 in front. The subtalar joint is composed of three articulation surfaces between the talus 102 and the calcaneum 104: the posterior facet (surfaces 1 and 5), the middle facet (surfaces 2 and 6) and the anterior facet (surfaces 3 and 4). The anterior and middle facets in some patients are touching and almost form one joint, in others (most) the two joints are separate with a small gap in between them.

The talus 102 acts as the load bearing fulcrum between the ankle and subtalar joint. Its dome articulates with the ankle, its head with the navicular and its under surface with the calcaneum 104 forming the subtalar joint. It is 60% covered in cartilage and gives rise to no muscle origin. It has a main blood supply running from anterior to posterior derived from the dorsalis pedis artery, medial deltoid and tarsal canal arteries.

The calcaneum 104 is a cancellous bone that forms the bony heel with its large posterior tuberosity. The load bearing posterior third of the bone is extra-articular and also acts a lever arm for its attachment of the gastrosoleus complex. When viewed from behind in plantigrade stance, the heel sits in 10-15 degrees of valgus with respect to the coronal axis of the leg. This alignment changes during gait. The middle third of the calcaneum is lined dorsally with hyaline articular cartilage and comprises the posterior facet of the subtalar joint. The posterior facet surface has a complex oblique orientation from posterolateral to anteromedial. When viewed along the oblique orientation axis, the calcaneum portion 1 of the posterior facet surface is convex. Perpendicular to this view the calcaneum portion 1 of the posterior facet surface is down-sloping and again convex posteriorly to anterior. This shape is reflected in the talar portion 5 of the posterior facet with which the posterior facet 1 of the calcaneum 104 engages, thereby forming a congruent subtalar joint.

The anterior third of the calcaneum 104 comprises the anterior 2 and middle 3 facets of the subtalar joint and the sustentaculum tali. These smaller facets are concave in an arc that is completed by the articular surface of the navicular approximating the socket of the "coxa pedis" in which sits the ball shaped talar head. The overlying anterior talus 102 is congruent with the calcaneum 104.

Short and stout interosseus talocalcaneal ligaments provide stability to the subtalar joint. They are most prominent in the sinus tarsi directly under the weight-bearing axis of the leg. In addition to providing stability, they provide a semi-controlled axis of motion for the joint and in this role they are sometimes regarded as analogous to the cruciates of the knee. Laterally and posteriorly are two thinner talocalcaneal ligaments which also play a supporting role. Kite's angle is the talocalcaneal angle in the frontal plane and represents the divergence of the respective longitudinal axes. Stance phase value of 17-21 degrees is considered normal. On the lateral image the calcaneal pitch is normally 20-25 degrees from the horizontal with a talar pitch very similar. The overall lateral talocalcaneal angle is a combined value at 30-50 degrees.

The medial talocalcaneal ligament extends from the medial tubercle of the talus 102 to the sustentaculum tali on the medial surface of the calcaneum 104. A synovial membrane lines the capsule of the joint, and the joint is wrapped in a capsule of short fibers that are continuous with the talocalconeonavicular and calcaneocuboid joints of the foot.

The subtalar joint and the ankle form a link between the long bones of the leg and the perpendicular construct of the foot. Movements of the ankle require reactionary changes in the subtalar and transverse tarsal joints for effective load transmission and propulsion. Movements of the subtalar joint are complex and differ with closed or open chain stages of gait. They accommodate irregularities in ground contact by unlocking the hind and midfoot during heel strike to stance phase. Subsequently the talar movements about the calcaneum 104 and navicular 106 draw the heel into varus and help supinate the foot, which creates a more rigid construct to allow propulsive power to be transmitted.

The changing talocalcaneal relationship plays a role in stabilising the ankle complex. The importance of this can sometimes be seen when the natural condition is disrupted by subtalar or triple fusion operations. After such operations the ankle can be subjected to coronal forces of varus and valgus that were previously absorbed in the hindfoot. This in turn can cause eventual talar tilt and accelerated wear with uneven joint space loss.

The inventors have recognised that the natural subtalar joint allows inversion and eversion of the foot via an internal and external motion of the talus 102 over the curved surface of the posterior facet 1 of the calcaneum 104 about a pivot point defined by the middle facet 2. The inventors have further recognised that the normal inversion and eversion of the subtalar joint (which is actually rotation) takes place mainly during non load bearing stance. In single legged midstance, the joint locks and minimal motion occurs. In the following description, embodiments of a subtalar joint implant 20 are disclosed that allow the natural function of the subtalar joint to be emulated in a realistic and reliable manner, based on the above understanding and using components that can be manufactured easily and in a commercially viable way.

FIGS. 5-8 illustrate the subtalar joint of FIGS. 1-4 with elements of a subtalar joint implant 20 according to an embodiment attached to the calcaneum 104 and talus 102. FIGS. 9-15 show the implant 20 in further detail.

The implant 20 is configured to replace the natural subtalar joint existing between the talus 102 and calcaneum 104 bones of a patient. The implant 20 comprises a talar portion 22. The talar portion 22 is configured to be rigidly attached to the talus 102. The implant 20 further comprises a calcaneal portion 24. The calcaneal portion 24 is configured to be rigidly attached to the calcaneum 104. In the following discussion the upper and lower directions are defined relative to the orientation of the implant 20 when implanted in a weight bearing (e.g. standing) patient.

Figure 11:
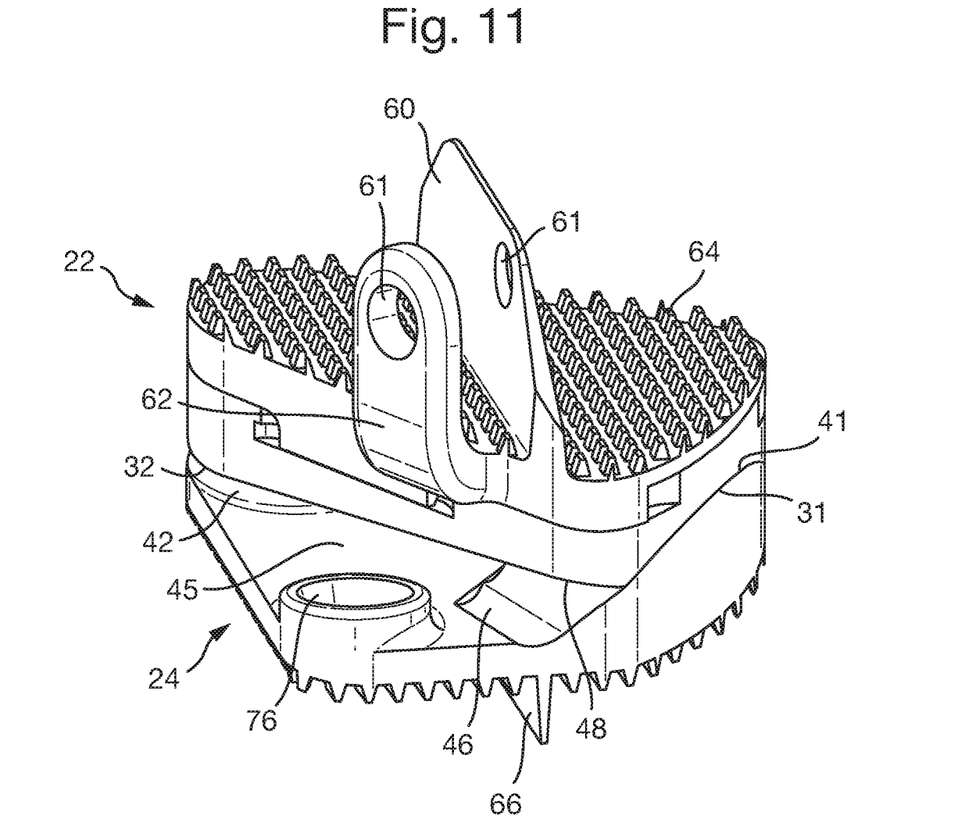
FIG. 11 depicts the talar and calcaneal portions of FIGS. 9 and 10 assembled together to form the subtalar implant as it will be configured in the implanted state.
Figure 12:
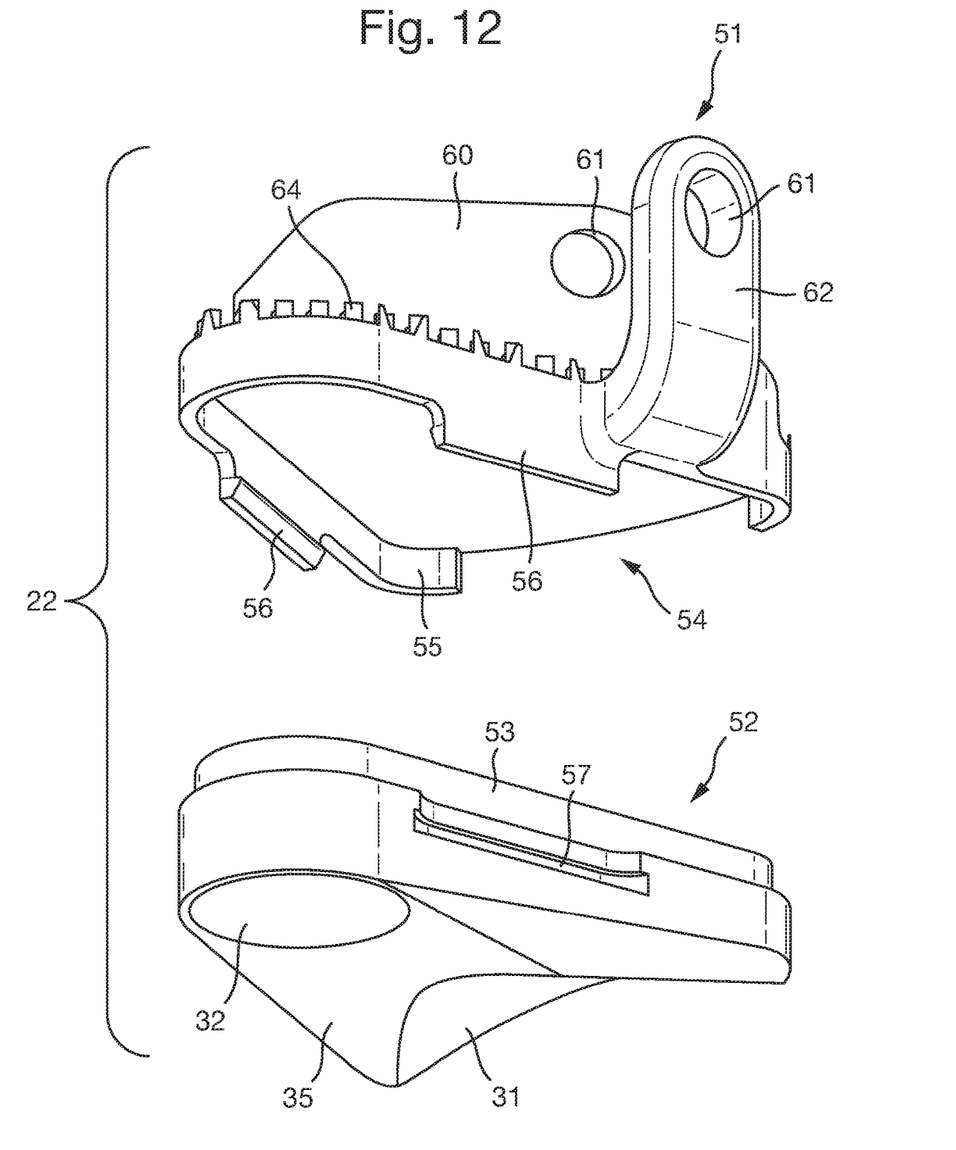
FIG. 12 depicts an alternative perspective exploded view of the upper and lower components of the talar portion shown in FIG. 9, showing undersides of the upper and lower components.

The talar portion 22 has a first region 31 on a lower surface of the talar portion 22 (see FIG. 12 for example). The talar portion 22 has a second region 32 on the lower surface of the talar portion 22. The calcaneal portion 24 has a first region 41 on an upper surface of the calcaneal portion 24 (see FIG. 10 for example). The calcaneal portion 24 has a second region 42 on the upper surface of the calcaneal portion 24. The first region 31 of the talar portion 22 is configured to be in contact with the first region 41 of the calcaneal portion 24 during use, as shown for example in FIG. 11. The second region 32 of the talar portion 22 is configured to be in contact with the second region 42 of the calcaneal portion 24 during use, as shown for example in FIG. 11.

Optionally, the first region 31 of the talar portion 22 is not in contact with any portion of the second region 42 of the calcaneal portion 24 in use. Optionally, the second region 32 of the talar portion 22 is not in contact with any portion of the first region 41 of the calcaneal portion 24 in use.

For example, the first and second regions 31,32,41,42 may be configured such that, throughout the allowed range of relative movement between the talar portion 22 and the calcaneal portion 24, there is always a continuous separating region 35 on the lower surface of the talar portion 22 that separates the first region 31 from the second region 32 throughout the allowed range of relative movement. The separating region 35 may be such that at no time throughout the allowed range of relative movement is the separating region 35 in contact with any part of the calcaneal portion 24.

For example, the first and second regions 31,32,41,42 may be configured such that, throughout the allowed range of relative movement between the talar portion 22 and the calcaneal portion 24, there is always a continuous separating region 45 on the upper surface of the calcaneal portion 24 that separates the first region 41 from the second region 42 throughout the allowed range of relative movement. The separating region 45 may be such that at no time throughout the allowed range of relative movement is the separating region 45 in contact with any part of the talar portion 22.

The first regions 31 and 41 are shaped so as to allow sliding of the first region 31 of the lower surface of the talar portion 22 over the first region 41 of the upper surface of the calcaneal portion 24.

In the embodiment shown, the second regions 32 and 42 are shaped so as to define a pivot point and to constrain the sliding of the first region 31 of the lower surface of the talar portion 22 over the first region 41 of the upper surface of the calcaneal portion 24 to trajectories that involve pivoting of the talar portion 22 relative to the calcaneal portion 24 about the pivot point. In other embodiments, the second regions 32 and 42 may be shaped so as to define a line (curved or straight) of pivot points and to constrain the sliding of the first region 31 of the lower surface of the talar portion 22 over the first region 41 of the upper surface of the calcaneal portion 24 to trajectories that involve pivoting of the talar portion 22 relative to the calcaneal portion 24 about one of a plurality of pivot points lying along the line of pivot points.

In an embodiment, the sliding of the first regions 31 and 41 relative to each other is along a curved trajectory. In the embodiment shown, the curved trajectory is provided by means of cooperation between the concave curved shape of the first region 31 (as shown for example in FIG. 12) and the convex curved shape of the first region 41 (as shown for example in FIG. 10). The sliding along a curved trajectory may imitate a sliding along a curved trajectory that occurs between the posterior facet 1 of the calcaneum 104 and the posterior facet 5 of the talus 102. The combination of the first regions 31 and 41 may therefore be seen as providing functionality that is the same or similar to the functionality that is provided by the combination of the posterior facets 1 and 5 of the calcaneum 104 and talus 102.

In an embodiment, the first surfaces 31 and 41 are configured such that the sliding of the first regions 31 and 41 relative to each other constitutes rotation of the talar portion 22 relative to the calcaneal portion 24 about an axis that is fixed during a portion or all of an allowed range of sliding. This rotation imitates rotation that is provided by the combination of the posterior facets 1 and 5 of the calcaneum 104 and talus 102 in the natural subtalar joint.

Figure 16:
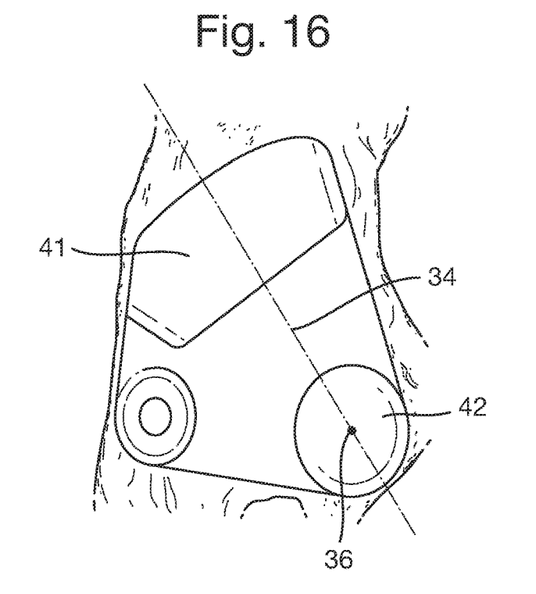
FIG. 16 is a top view of an example calcaneal portion in the implanted state, illustrating a representative axis about which rotation of the talar portion can occur and a representative pivot point about which pivoting of the talar portion can occur.
Figure 17:
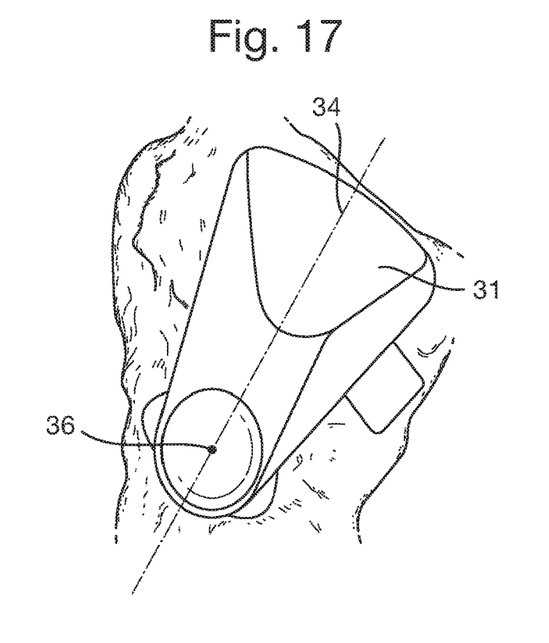
FIG. 17 is a bottom view of an example talar portion compatible with the calcaneal portion of FIG. 16, illustrating the axis of rotation and pivot point shown in FIG. 16.
Figure 18:
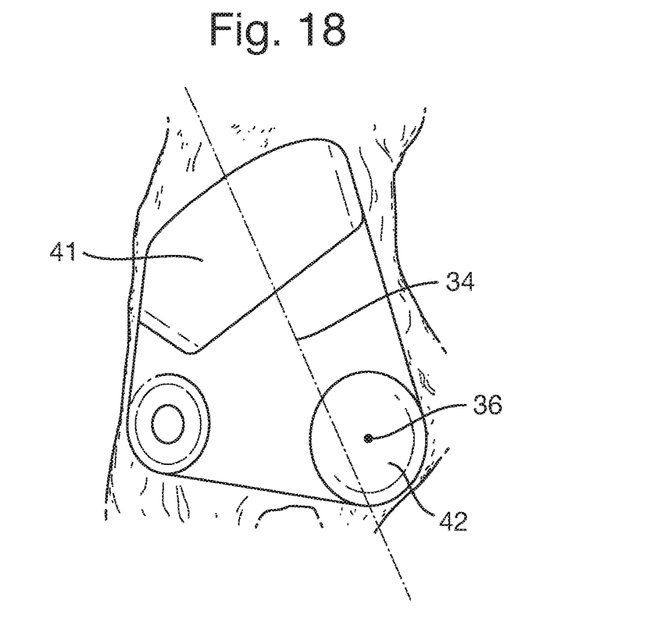
FIG. 18 depicts an arrangement that is the same as that shown in FIG. 16 except that the axis of rotation does not pass exactly through the pivot point.
Figure 19:
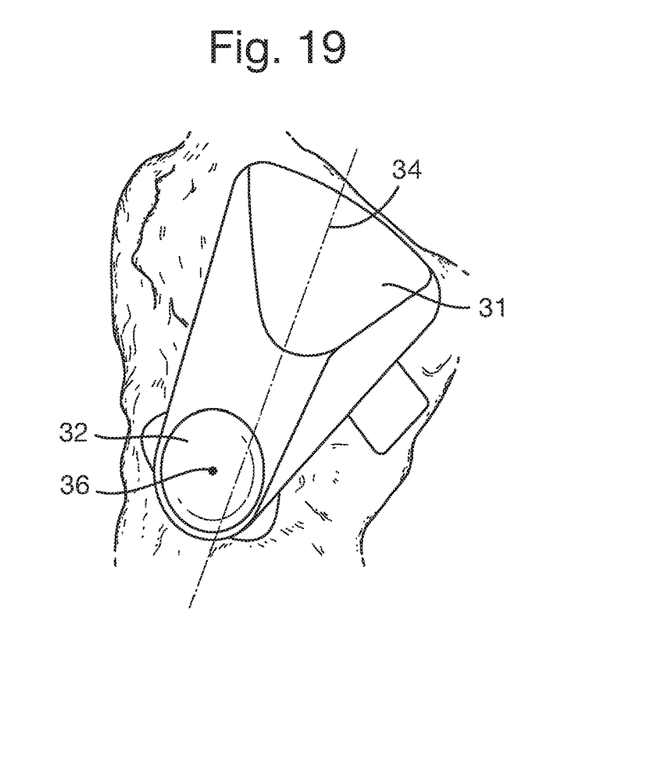
FIG. 19 is a bottom view of an example talar portion compatible with the calcaneal portion of FIG. 18, illustrating the axis of rotation and pivot point shown in FIG. 18.

In an embodiment, as shown for example in FIGS. 16 and 17, when viewed from above, the axis of rotation 34 passes through the pivot point 36 (or, in other embodiments, through the line of pivot points, where a line of pivot points is provided). Alternatively, as shown for example in FIGS. 18 and 19, the axis of rotation 34 may pass through a region adjacent to the pivot point that overlaps with one or both of the second regions 32 and 42. Alternatively, the axis of rotation 24 may pass through a region adjacent to the line of pivot points, where a line of pivot points is provided, the region overlapping with one or both of the second regions 32 and 42.

Figure 10:
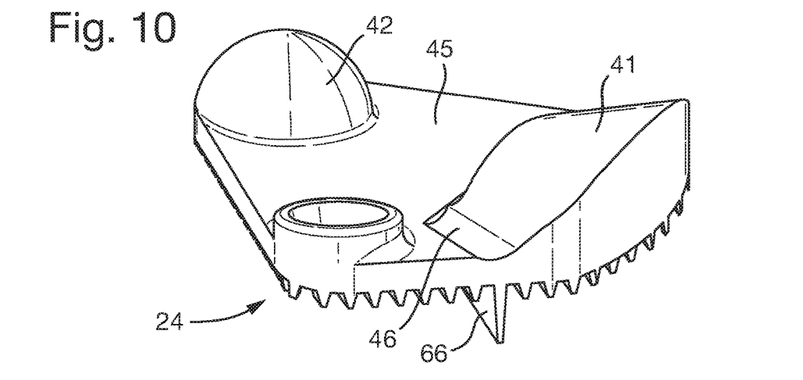
FIG. 10 depicts a perspective view of a calcaneal portion of the example subtalar implant of FIG. 9.

In an embodiment, one of the first regions 31 and 41 of the lower and upper surfaces comprises a portion of an external surface of a frustum. In such an embodiment, the other of the first regions of the lower and upper surfaces may comprise a portion of an internal surface of a frustum, optionally the same frustum. In the particular example shown in FIGS. 10 and 12, the first region 31 of the lower surface of the talar portion 22 comprises a portion of the internal surface of a frustum (i.e. is concave). As shown in FIG. 10, for example, the first region 41 of the upper surface of the calcaneal portion 24 comprises a portion of the external surface of a frustum (i.e. is convex). In other embodiments, the geometries may be reversed, with the first region 31 of the lower surface of the talar portion 22 having a convex form (e.g. a portion of an external surface of a frustum) and the first region 41 of the upper surface of the calcaneal portion 24 having a concave form (e.g. a portion of an internal surface of a frustum).

In an embodiment, one of the second regions 32 and 42 comprises a ball-like protrusion and the other of the second regions 42 and 32 comprises a cup-like depression. The resulting arrangement may be referred to as a ball and socket joint. A ball-like protrusion is generally rounded and could for example comprise a portion that forms part of an approximate sphere. A cup-like depression is generally rounded and could for example comprise a portion that forms part of an approximate sphere. FIGS. 10 and 12 show an embodiment in which the second region 32 of the talar portion 22 comprises a cup-like depression and the second region 42 of the calcaneal portion 24 comprises a ball-like protrusion. In other embodiments, the geometries may be reversed, with the second region 32 of the lower surface of the talar portion 22 having a ball-like protrusion and the second region 42 of the upper surface of the calcaneal portion 24 having a cup-like depression.

Figure 20:
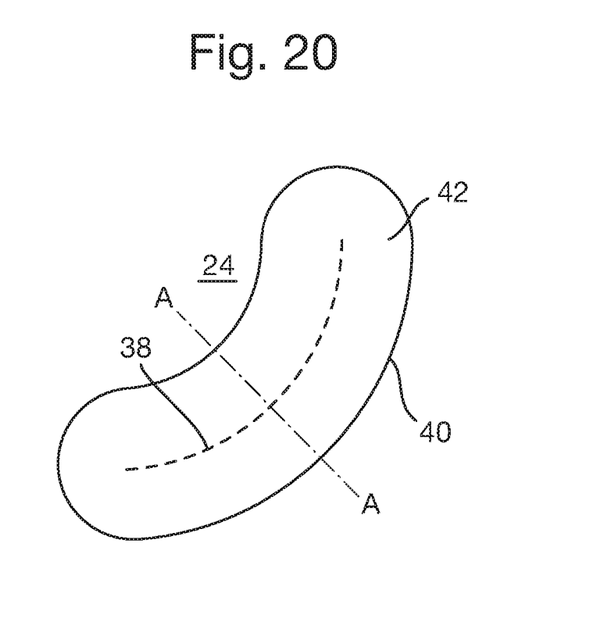
FIG. 20 is a schematic top view of a second region comprising a channel with a rounded base, the channel allowing pivoting of a talar portion about a calcaneal portion about one or more of a plurality of different pivot points on a line of pivot points.
Figure 21:
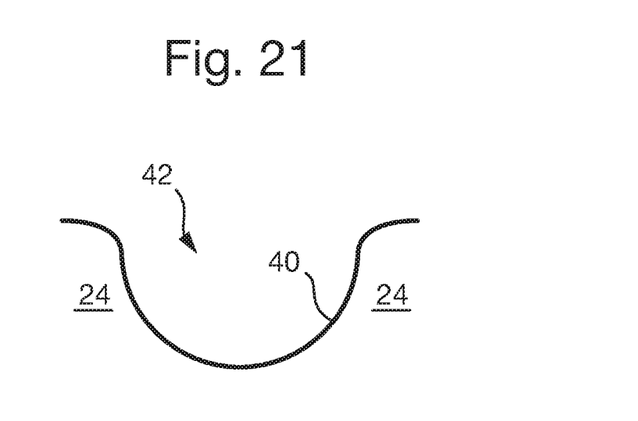
FIG. 21 is a schematic side sectional view along line A-A in FIG. 20.

In an alternative embodiment, one of the second regions comprises a ball-like protrusion and the other of the second regions comprises a channel with a rounded base. An example of a channel 40 with a rounded base is shown in FIG. 20. Such a channel 40 could be formed in the talar portion 22 instead of the cup-like depression in the example shown in FIG. 12. Such a channel 40 could cooperate with a second region 42 comprising a ball-like protrusion such as that shown in the example of FIG. 10. The cooperation between such a channel 40 and a ball-like protrusion could allow pivoting of the talar portion 22 about the calcaneal portion 24 about one or more pivot points along a line 38 of pivot points.

In an embodiment, the talar portion 22 comprises an upper component 51 and a lower component 52. The upper component 51 is configured to be rigidly attached to the talus 102. The lower component 51 presents the lower surface of the talar portion 22. The lower component 52 is formed from a material having a lower coefficient of friction than the upper component 51. For example, the upper component 51 may be formed from a metal and the lower component 52 may be formed from a plastic or a ceramic material or another type of material that has the required lower coefficient of friction than the metal. In such an embodiment, the upper surface of the calcaneal portion 24 may be formed from a metal. FIG. 12 shows an example configuration of the upper and lower components 51 and 52. In this particular example the lower component 52 is provided with a recessed region 53 that is configured to fit within a space 54 provided on a lower portion of the upper component 51. A rim 55 engages against the laterally outer borders of the recessed region 53 and provides lateral stability to the connection. An engaging tongue 56 is provided for engaging with a corresponding groove 57 to connect the upper and lower components 51 and 52 together, for example in the manner of a snap-fitting connection.

In other embodiments, the calcaneal portion 24 may comprise a lower component configured to be rigidly attached to the calcaneum 104 and an upper component that presents the upper surface of the calcaneal portion 24, the upper component being formed from a material having a lower coefficient of friction than the lower component. For example, the lower component may be formed from a metal and the upper component may be formed from a plastic or a ceramic material or another type of material that has the required lower coefficient of friction than the metal. In such an embodiment, the lower surface of the talar portion 22 may be formed from a metal.

The combination of the materials of the upper surface of the calcaneal portion 24 and the lower surface of the talar portion 22, at least in the first and second regions 31,32,41, 42 where the upper and lower surfaces are in contact with each other, should be such as to provide 1) an appropriate level of friction in both the loaded and unloaded states, and 2) appropriate longevity (e.g. suitably low wearing rate). The level of friction may be arranged to be similar to the level of friction encountered between the corresponding facets of the talus 102 and calcaneum 104 in the natural subtalar joint.

In an embodiment, the materials and shapes of the first regions 31 and 41 are configured such that the sliding of the first regions 31 and 41 relative to each other is substantially prevented by friction between the first regions 31 and 41 when 10% or more of the patient's weight is applied between the talar and calcaneal portions 22 and 24. For example, friction may be arranged to be such that sliding is very difficult or impossible for an average patient to effect while applying the 10% or more of the patient's weight.

In an embodiment, the talar portion 22 or the calcaneal portion 24 comprises one or more abutment members 46 configured to restrict the sliding of the first regions 31 and 41 relative to each other to within a predetermined range. Where the sliding of the first regions 31 and 41 relative to each other constitutes rotation of the talar portion 22 relative to the calcaneal portion 24, the one or more abutment members 46 may be configured to restrict the rotation to a range of 40 degrees or less.

In an embodiment, as shown for example in FIG. 11, the calcaneal portion 24 comprises at least one of the abutment members 46 and the talar portion 22 is configured to be brought into contact with one of the abutment members 46 of the calcaneal portion 24 at one or both extreme ends of the predetermined range of sliding of the first regions 31 and 41 relative to each other. In the example of FIG. 11, for example, it can be seen that if the talar portion 22 were to be slid in an anticlockwise sense (for the particular device shown in FIG. 11 and as viewed in FIG. 11) a portion 48 of the lower surface of the talar portion 22 would eventually be brought into abutment against the abutment member 46. The bringing into abutment of the portion 48 with the abutment member 46 would prevent any further rotation in the anticlockwise direction and therefore defines the range of possible rotation in the anticlockwise sense. A corresponding abutment member 46 is provided on the other side of the first region 41 and will limit a range of possible rotation in the opposite sense by abutment of a corresponding portion 48 of the lower surface of the talar portion 22 with the corresponding abutment member 46. The provision of such abutment members 46 limits the range of rotation that is allowed, in a similar manner to the way that movement is limited in the natural subtalar joint. The risk of injury to surrounding anatomy by excessive movement is therefore reduced.

In an alternative embodiment, the talar portion 22 may comprises at least one of the abutment members 46 and the calcaneal portion 24 may be configured to be brought into contact with one of the abutment members 46 of the talar portion 22 at one or both extreme ends of the predetermined range of sliding of the first regions 31 and 41 relative to each other.

In an embodiment, the talar portion 22 and the calcaneal portion 24 are configured to be implanted in such a way that, when viewed from above, the first regions 31 and 41 overlap with a region where the posterior facet of the subtalar joint (e.g. the posterior facet 1 of the calcaneum 104, the posterior facet 5 of the talus 102, or both) was located prior to implantation of the implant 20. This can be seen to be the case in the embodiment shown in FIGS. 5-8 (compare for example FIG. 5 with FIG. 1).

In an embodiment, the talar portion 22 and the calcaneal portion 24 are configured to be implanted in such a way that, when viewed from above, the second regions 32 and 42 overlap with a region where the middle facet of the subtalar joint (e.g. the middle facet 2 of the calcaneum 204, the middle facet 6 of the talus 102, or both) was located prior to implantation of the implant 20. Preferably, the second regions 32 and 42 overlap with a central point of the middle facet.

An example methodology for implanting a subtalar joint implant 20 is described below.

First, an implant 20 according to an embodiment is provided. The implant 20 may be one of the examples discussed above or any other embodiment falling within the scope of the claims.

Secondly, a space is prepared between the talus 102 and the calcaneum 104 that is suitable for accommodating the implant 20. The space may be prepared by cutting a region out of the bone in either or both of the talus 102 and the calcaneum 104.

Thirdly, the implant 20 is implanted in the space in such a way that, when viewed from above, the first regions 31 and 41 overlap with a region where the posterior facet of the subtalar joint (e.g. the posterior facet 1 of the calcaneum 104, the posterior facet 5 of the talus 102, or both) was located prior to implantation of the implant 20 and the second regions 32 and 42 overlap with a region where the middle facet of the subtalar joint (e.g. the middle facet 2 of the calcaneum 204, the middle facet 6 of the talus 102, or both) was located prior to implantation of the implant 20.

In an example method a probe may be used to identify a central point of either or both of the middle facets 2 and 6. The identified central point is then used as a reference to make the bony cuts. Once the surfaces are cut a trial implant may be placed in situ and then the hindfoot will be moved from side to side (inversion/eversion) a few times to allow the implant to settle to the best fit position. The trial implant or an associated jig may then be pinned and used as a reference to position the relevant portion of the final implant 20 (i.e. the part of the talar portion 22 that is to be fixed to the bone or the part of the calcaneal portion 24 that is to be fixed to the bone).

Various fixation features may be provided on the talar portion 22 and on the calcaneal portion 24 to allow the portions 22 and 24 to be fixed rigidly and reliability to the bones of the talus 102 and calcaneum 104.

The following fixation features are provided in the example embodiment shown in FIGS. 9-15.

Figure 9:
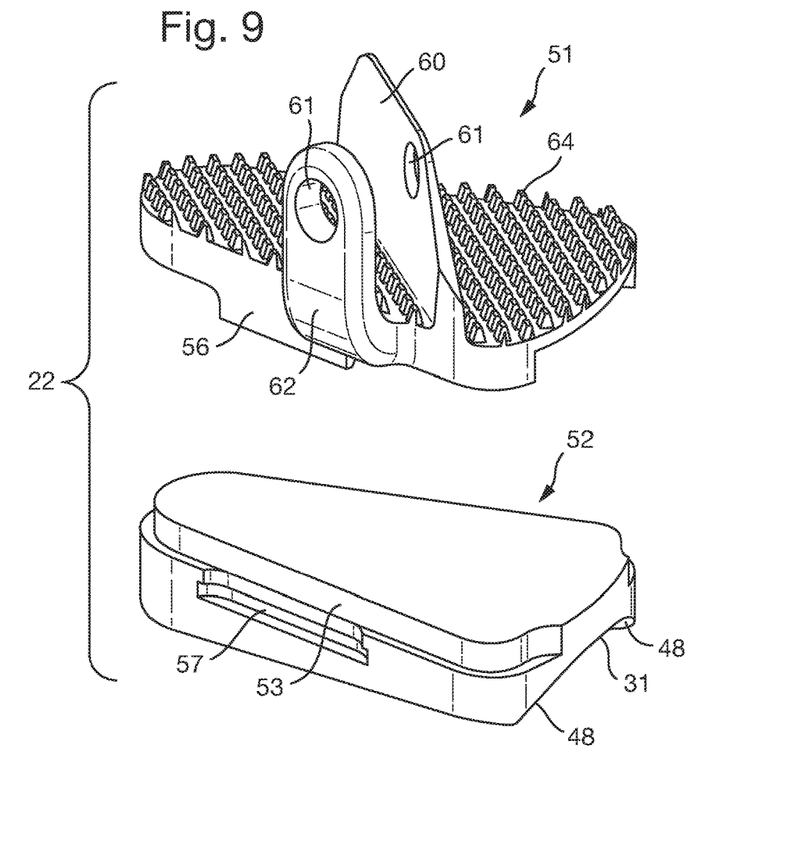
FIG. 9 depicts a perspective exploded view of upper and lower components of a talar portion of an example subtalar implant.

As shown in FIG. 9, for example, the talar portion 22 may be provided with a rigid fin 60 and a side arm 62 (in the particular example shown, where the talar portion is formed from an upper component 51 and a lower component 52, these features are provided in the upper component 51). The rigid fin 60 may narrow in a direction of insertion (upwards in the Figures), to facilitate insertion. The rigid fin 60 may also comprise a fixation hole 61 to allow traversal of the rigid fin 60 by a fixing member such as a screw, bolt or pin. The rigid fin 60 has an elongate cross-section when viewed from above, thereby providing stability to the implant. The side arm 62 also comprises a fixation hole 61 to allow traversal of the side arm 62 by a fixing member such as a screw, bolt or pin. The talar portion 22 further comprises a surface structure comprising a plurality of protrusions 64 extending upwards. In the implanted state, the protrusions 64 extend into the bone and help to prevent slippage occurring between the talar portion 22 and the talus 102.

Figure 13:
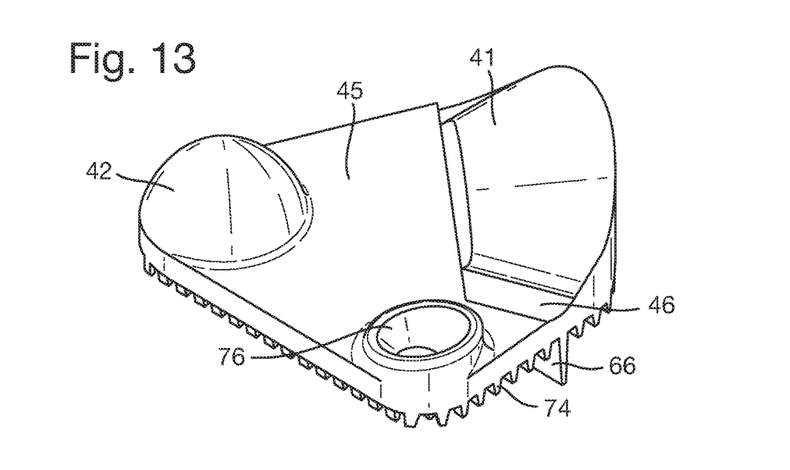
FIG. 13 depicts a perspective view from above of a calcaneal portion of an example subtalar implant.
Figure 14:
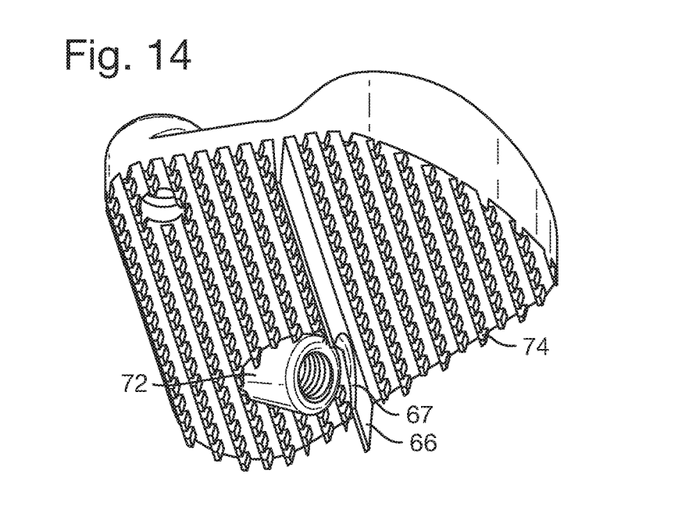
FIG. 14 depicts a perspective view from below of the calcaneal portion of FIG. 13.
Figure 15:
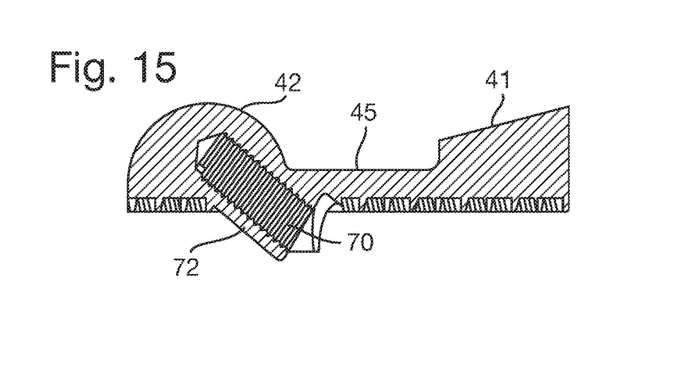
FIG. 15 depicts a side sectional view through a central region of the calcaneal portion shown in FIGS. 13 and 14.

As shown in FIGS. 13 and 14, for example, the calcaneal portion 24 may also comprise a rigid fin 66 on the surface that is to engage against the bone of the calcaneum 24 (the lower surface of the calcaneal portion 24). The rigid fin 66 may comprise a fixation hole 61 (or, in the example shown, a fixation cut-out 67) to allow traversal of the rigid fin 66 by a fixing member 70 such as a screw, bolt or pin (a screw 70 engaging in a threaded hole 72 in the example shown). The rigid fin 66 has an elongate cross-section when viewed from above, thereby providing stability to the implant 20 in the implanted state. The calcaneal portion 24 may further comprise a surface structure comprising a plurality of protrusions 74 extending downwards. In the implanted state, the protrusions 74 extend into the bone and help to prevent slippage occurring between the calcaneal portion 24 and the calcaneum 104. In an embodiment, the calcaneal portion 24 comprises a further fixation hole 76 configured to allow traversal of the calcaneal portion by a fixing member such as a screw, bolt or pin, for fixing the calcaneal portion to the calcaneum 104.

The invention claimed is:

1. A subtalar joint implant for replacing a natural subtalar joint existing between the talus and calcaneum bones of a patient, the implant comprising:
    a talar portion configured to be rigidly attached to the talus; and a calcaneal portion configured to be rigidly attached to the calcaneum, wherein, where upper and lower directions are defined relative to the orientation of the implant when implanted in a weight bearing or standing patient:

a first and a second region of a lower surface of the talar portion are configured to be in contact with respective first and second regions of an upper surface of the calcaneal portion during use;

the first regions are shaped so as to allow sliding of the first region of the lower surface of the talar portion over the first region of the upper surface of the calcaneal portion; and the second regions are shaped so as to define a pivot point or line of pivot points and constrain said sliding of the first region of the lower surface of the talar portion over the first region of the upper surface of the calcaneal portion to trajectories that involve pivoting of the talar portion relative to the calcaneal portion about the pivot point or pivot points.

2. The implant of claim 1, wherein the sliding of the first regions relative to each other is along a curved trajectory.

3. The implant of claim 1, wherein the sliding of the first regions relative to each other constitutes rotation of the talar portion relative to the calcaneal portion about an axis that is fixed during a portion or all of an allowed range of sliding.

4. The implant of claim 3, wherein, when viewed from above, said axis passes through said pivot point, passes through said line of pivot points, passes through a region adjacent to the pivot point that overlaps with one or both of the second regions, or passes through a region adjacent to said line of pivot points that overlaps with one or both of the second regions.

5. The implant of claim 1, wherein one of the first regions of the lower and upper surfaces comprises a portion of an external surface of a frustum.

6. The implant of claim 5, wherein the other of the first regions of the lower and upper surfaces comprises a portion of an internal surface of a frustum.

7. The implant of claim 1, wherein one of the second regions comprises a ball-like protrusion and the other of the second regions comprises a cup-like depression or a channel with a rounded base.

8. The implant of claim 1, wherein the talar portion comprises an upper component configured to be rigidly attached to the talus and a lower component that presents the lower surface of the talar portion, the lower component being formed from a material having a lower coefficient of friction than the upper component.

9. The implant of claim 8, wherein the upper component is formed from metal and the lower component is formed from plastic or ceramic.

10. The implant of claim 8, wherein the upper surface of the calcaneal portion is formed from a metal.

11. The implant of claim 1, wherein the calcaneal portion comprises a lower component configured to be rigidly attached to the calcaneum and an upper component that presents the upper surface of the calcaneal portion, the upper component being formed from a material having a lower coefficient of friction than the lower component.

12. The implant of claim 11, wherein the lower component is formed from metal and the upper component is formed from plastic or ceramic.

13. The implant of claim 11, wherein the lower surface of the talar portion is formed from a metal.

14. The implant of claim 1, wherein the talar portion or the calcaneal portion comprises one or more abutment members configured to restrict the sliding of the first regions relative to each other to within a predetermined range.

15. The implant according to claim 14, wherein the sliding of the first regions relative to each other constitutes rotation of the talar portion relative to the calcaneal portion and the one or more abutment members are configured to restrict the rotation to a range of 40 degrees or less.

16. The implant of claim 14, wherein the talar portion comprises at least one of the abutment members and the calcaneal portion is configured to be brought into contact with one of the abutment members of the talar portion at one or both extreme ends of the predetermined range of sliding of the first regions relative to each other.

17. The implant of claim 14, wherein the calcaneal portion comprises at least one of the abutment members and the talar portion is configured to be brought into contact with one of the abutment members of the calcaneal portion at one or both extreme ends of the predetermined range of sliding of the first regions relative to each other.

18. The implant of claim 1, wherein the talar and calcaneal portions are configured to be implanted in such a way that, when viewed from above, the first regions overlap with a region where the posterior facet of the subtalar joint was located prior to implantation of the implant.

19. The implant of claim 1, wherein the talar and calcaneal portions are configured to be implanted in such a way that, when viewed from above, the second regions overlap with a region where the middle facet of the subtalar joint was located prior to implantation of the implant.

20. A method of implanting a subtalar joint implant for replacing a natural subtalar joint existing between the talus and calcaneum bones of a patient, wherein the implant comprises:

a talar portion configured to be rigidly attached to the talus; and a calcaneal portion configured to be rigidly attached to the calcaneum, wherein, where upper and lower directions are defined relative to the orientation of the implant when implanted in a weight bearing or standing patient:

a first and a second region of a lower surface of the talar portion are configured to be in contact with respective first and second regions of an upper surface of the calcaneal portion during use;

the first regions of the lower and upper surfaces are shaped so as to allow sliding of the first region of the lower surface over the first region of the upper surface; and the second regions of the lower and upper surfaces are shaped so as to define a pivot point or line of pivot points and constrain said sliding of the first region of the lower surface over the first region of the upper surface to trajectories that involve pivoting of the talar portion relative to the calcaneal portion about the pivot point or pivot points, wherein the method comprises:

preparing a space between the talus and calcaneum that is suitable for accommodating the implant;

implanting the implant in the space in such a way that, when viewed from above, the first regions overlap with a region where the posterior facet of the subtalar joint was located prior to implantation of the implant and the second regions overlap with a region where the middle facet of the subtalar joint was located prior to implantation of the implant.

* * * * *